United States Patent
Camisani et al.

(10) Patent No.: US 10,562,041 B2
(45) Date of Patent: Feb. 18, 2020

(54) DEVICE, SYSTEM AND METHOD FOR THE CONTINUOUS PROCESSING AND SEPARATION OF BIOLOGICAL FLUIDS INTO COMPONENTS

(71) Applicant: Biosafe S.A., Eysins (CH)

(72) Inventors: Julien Pierre Camisani, Denens (CH); Yannick Andre Sublet, Nyon (CH); Pau Mato Sabat, Divonne-les-Bains (FR)

(73) Assignee: Biosafe S.A., Eysins (CH)

( * ) Notice: Subject to any disclaimer, the term of this patent is extended or adjusted under 35 U.S.C. 154(b) by 9 days.

(21) Appl. No.: 15/569,270

(22) PCT Filed: Jan. 11, 2016

(86) PCT No.: PCT/IB2016/050107
§ 371 (c)(1),
(2) Date: Oct. 25, 2017

(87) PCT Pub. No.: WO2016/178100
PCT Pub. Date: Nov. 10, 2016

(65) Prior Publication Data
US 2018/0111133 A1 Apr. 26, 2018

(30) Foreign Application Priority Data
May 7, 2015 (CH) ........................... 0627/15

(51) Int. Cl.
*B04B 5/04* (2006.01)
*A61M 1/36* (2006.01)
(Continued)

(52) U.S. Cl.
CPC ......... *B04B 5/0442* (2013.01); *A61M 1/3696* (2014.02); *A61M 1/3698* (2014.02);
(Continued)

(58) Field of Classification Search
CPC . A61M 1/3696; A61M 1/3698; B04B 5/0442; B04B 11/02; B04B 11/06; B04B 2005/0485
See application file for complete search history.

(56) References Cited

U.S. PATENT DOCUMENTS

| 3,104,225 A | 8/1963 | Bendetto |
| 3,145,713 A | 8/1964 | Latham, Jr. |

(Continued)

FOREIGN PATENT DOCUMENTS

| CN | 204234222 U | 4/2015 |
| EP | 0912250 B1 | 11/1999 |

(Continued)

OTHER PUBLICATIONS

Singapore Written Opinion and Search Report from Singapore Appl. No. 11201708234X, dated Oct. 19, 2018, 7 pages.

(Continued)

*Primary Examiner* — Timothy C Cleveland
(74) *Attorney, Agent, or Firm* — Wood IP LLC

(57) ABSTRACT

A device for the processing and separation of biological fluids into components comprises a hollow centrifugal processing chamber (10) fitted with an inlet/outlet head (20) and preferably with an axially movable piston (18). The inlet/outlet head has two separate inlets/outlets, for instance an axial inlet (29) and a lateral outlet (40). The processing chamber (1) is fitted with an internal flow guide (30) enabling operation of the device in a continuous processing mode wherein biological fluid to be processed is continuously intaken by say the axial inlet (29) and at the same time processed components are continuously removed via say the lateral outlet (40). The continuous processing flow can be driven by an external peristaltic pump (59) and/or by axial displacement of a piston (18) in the chamber (10).

20 Claims, 12 Drawing Sheets

(51) Int. Cl.
*B04B 11/02* (2006.01)
*B04B 11/06* (2006.01)

(52) U.S. Cl.
CPC .............. *B04B 11/02* (2013.01); *B04B 11/06* (2013.01); *B04B 2005/0485* (2013.01)

(56) References Cited

U.S. PATENT DOCUMENTS

| | | | | |
|---|---|---|---|---|
| 3,565,330 | A | * | 2/1971 | Latham, Jr. ........... B04B 5/0442 277/380 |
| 6,629,919 | B2 | * | 10/2003 | Egozy ................... B04B 5/0442 494/36 |
| 8,070,666 | B2 | | 12/2011 | Rochat |
| 2007/0213191 | A1 | | 9/2007 | Chammas |

FOREIGN PATENT DOCUMENTS

| | | |
|---|---|---|
| EP | 1144026 B1 | 7/2004 |
| EP | 1800754 A1 | 6/2007 |
| GB | 2181371 B | 9/1989 |
| RU | 2455078 C1 | 7/2012 |
| WO | WO96/11747 | 4/1996 |
| WO | 2009/131659 A1 | 10/2009 |

OTHER PUBLICATIONS

Office Action +Search Report Received for Russian Patent Application No. 2017139944/05(069450), dated Mar. 25, 2019, Pages (5 Page of English Translation +6 Pages Official Copy).
Office Action for Chinese Patent Appl. No. 201680026370.X, filed Jan. 11, 2016, dated Feb. 26, 2019.

* cited by examiner

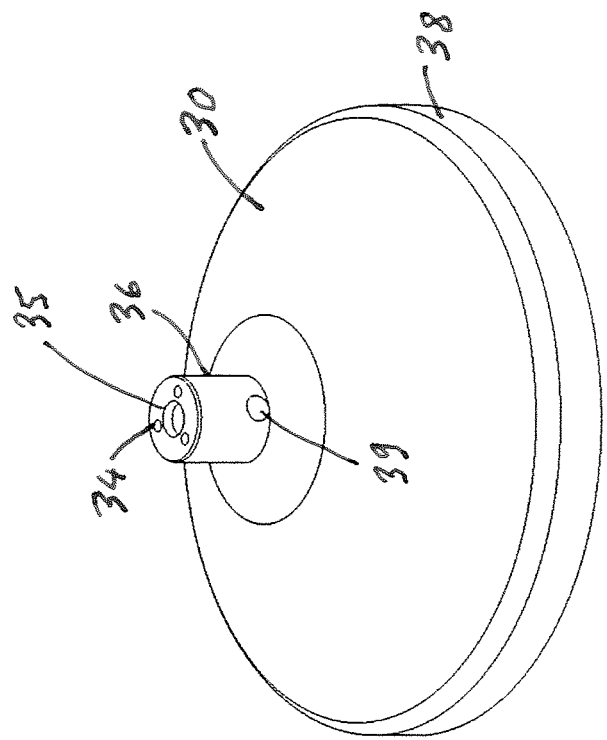
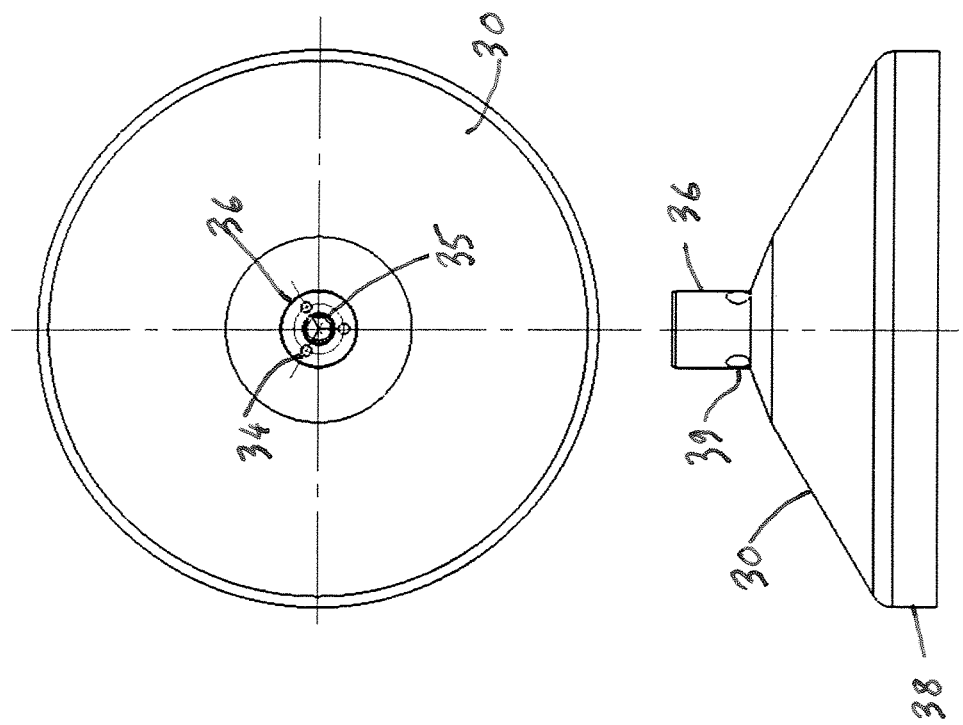
FIG. 2

Drawing 7: flow chart-main application

DEVICE, SYSTEM AND METHOD FOR THE CONTINUOUS PROCESSING AND SEPARATION OF BIOLOGICAL FLUIDS INTO COMPONENTS

FIELD OF THE INVENTION

This invention relates to a device, a system and a method for the processing and separation of biological fluids into components.

BACKGROUND OF THE INVENTION

The invention relates in particular to a device, a system and a method for the processing and separation of biological fluids into components of the type known from EP-B-0 912 250 and EP-B-1 144 026. Such known devices comprise a hollow centrifugal processing chamber rotatable about an axis of rotation. The processing chamber usually has an inner cylindrical wall enclosing a space for receiving biological fluids to be processed and having an inclined upper wall leading to a neck with an inlet/outlet for biological fluid to be processed and for processed components of the fluid. The space in the hollow processing chamber for receiving biological fluids occupies the entire volume across the hollow processing chamber between facing parts of the inner cylindrical wall and along the length of the cylindrical wall, said space having a given volume delimited by a bottom of the hollow cylindrical chamber, or a variable volume delimited by the position of an axially movable member within the cylindrical wall. The device also comprises a dynamic/static inlet/outlet head or "rotary seal" mounted on the neck of the processing chamber. The inlet/outlet head has a first part rotatable with the processing chamber and a second part that remains stationary. The first and second parts of the inlet/outlet head have a sealing means allowing rotation of the first part relative to the second part. The inlet/outlet head has a central through-passage for the inlet of biological fluid to be processed and the outlet of processed/separated components of the fluid.

Typically the centrifugal processing chamber contains within its cylindrical wall an axially movable member such as a piston that defines a separation space of variable volume wherein the biological fluid to be processed and separated is received. By axially moving this member, biological fluids can be intaken or output.

This known device forms part of a system wherein the processing chamber is part of a disposable set comprising a plurality of containers for receiving on the one hand the biological fluid to be processed and separated and, on the other hand, the separated components, and optionally one or more additional containers for additive solutions.

The known device and system are suitable for processing and separating many types of biological fluids including whole blood, apheresis blood, bone marrow blood and expanded cells or stem cells. However, the quantity of biological fluid that can be processed/separated at one time is limited by the maximum volume of the processing chamber's separation space. Therefore, in order to process large volumes of biological fluids with this known device and system, it is necessary to resort to using multiple disposable sets one after another in a single apparatus, or to run several disposable sets in parallel in multiprocessing apparatus.

Other devices for processing and separating biological fluids are known, but their structure is incompatible with that of EP-B-1 144 026 and they do not achieve the same advantages as EP-B-1 144 026. For example WO 2012/137086 describes a blood centrifugal device with a rotatable inner bowl disposed within a rotatable housing defining therebetween a narrow gap for receiving the blood being processed. A stationary structure is disposed in a central recess along the central axis of the device for delivering blood from an inlet at the top to the bottom where it passes into the bottom end of the narrow gap. At the top of the gap a separator separates blood components.

SUMMARY OF THE INVENTION

An object of the invention is to overcome the mentioned limitation of the known device/system EP-B-1 144 026 by proposing along the following lines an improved portable device working in combination with a disposable centrifugal processing chamber that has the capacity to sediment and separate biological fluid components from a large volume quantity of a biological fluid, including whole blood, apheresis blood, bone marrow blood and expanded cells or stem cells through culturing techniques, down to a very small quantity of volume, by combining a continuous processing flow mechanism advantageously with a variable size processing chamber through displacement of an axially movable element such as a piston.

According to one aspect of the invention there is provided a device of the above-mentioned type which further comprises a flow guide inserted in and rotatable with the processing chamber, the flow guide being located adjacent to, spaced slightly apart from and in shape-matching relationship to the inclined upper wall of the processing chamber to define with the inclined upper wall of the processing chamber an inclined, preferably annular, flow passage, the flow guide being disposed above said space for receiving biological fluids to be processed with its inclined flow passage leading into a top part of the inner cylindrical wall of the processing chamber.

In this improved device, the inlet/outlet head comprises a first inlet/outlet and a second inlet/outlet, the first and second inlets/outlets being disposed on the stationary second part of the inlet/outlet head at a top end and/or at a lateral side thereof, as well as an axial separator in the central through-passage of the inlet/outlet head, the axial separator defining separate first and second axially-directed passages in the inlet/outlet head.

An upper part of one of the first and second axially-directed passages communicates with one of the first and second inlets/outlets, and an upper part of the other of the first and second axially-directed passages communicates with the other of the first and second inlets/outlets. Moreover, a lower part of one of the first and second axially-directed passages communicates with said space in the processing chamber for receiving biological fluids to be processed, and a lower part of the other of the first and second axially-directed passages communicates with the inclined flow passage between the flow guide and the inclined upper wall of the processing chamber.

The inventive device is so arranged that it is operable in a continuous flow mode in which biological fluid to be processed can be inlet via one of the first and second inlets/outlets, while processed biological fluid is simultaneously outlet via the other of the first and second inlets/outlets.

In one embodiment, the axial separator is a central tube extending through the central through-passage of the inlet/outlet head, the central tube being connected (i) to deliver incoming biological fluid through the inside of the central tube and through the space between the flow guide and said inclined upper wall of the processing chamber, to the inner cylindrical wall of the processing chamber, and (ii) to extract processed fluid components separated at said inclined wall of the processing chamber and that pass through the space between the flow guide and said inclined upper wall of the processing chamber.

In this improved device, an inside part of the processing chamber located beyond (i.e. below) the flow guide can for example be in fluid communication via an aperture in the flow guide to the central through-passage of the inlet/outlet head outside said central tube of the inlet/outlet head; and the stationary second part of the inlet/outlet head has an outlet for the extraction of processed biological fluid components from the inside of the processing chamber, said outlet being in fluid communication with said central through-opening of the inlet/outlet head outside said central tube.

In one embodiment, the stationary second part of the inlet/outlet head comprises an external generally cylindrical body, and said outlet is a lateral outlet located in a lateral side of the generally cylindrical body. In this embodiment, the processing chamber can have an upwardly-projecting elongated central neck that extends into the inside of the rotatable first part of the inlet/outlet head up to adjacent the level of the lateral outlet. Also, in this case, the sealing means of the inlet/outlet head can comprise a first seal located axially on one side of the lateral outlet and a second seal located axially on the other side of the lateral outlet.

The axial separator such as a central tube can comprise a stationary axially-outer part extending in the stationary second part of the inlet/outlet head, and a rotatable axially-inner part connected to a central part of the flow guide for rotation therewith. In this embodiment the inner part of the central tube communicates with the space between the flow guide and the inclined upper wall of the processing chamber.

The rotatable first part of the inlet/outlet is typically located inside the stationary second part of the inlet/outlet head. The first inlet/outlet is typically an axial inlet/outlet on the inlet/outlet head and the second inlet/outlet is on a lateral side of the inlet/outlet head.

In a particular embodiment of the device: (i) the inclined upper wall of the processing chamber is frusto-conical as is the upper surface of the flow guide or diverter/inverter; (ii) the flow guide has a central sleeve that fits in the neck of the processing chamber leaving a space of several millimeters between the facing frusto-conical surfaces; (iii) the lower end of a central tube forming the axial separator fits in the central sleeve of the flow guide and communicates with said space between the facing frusto-conical surfaces; and (iv) said aperture in the flow guide is in the form of at least one through passage, preferably three equally-distributed through passages, in its central sleeve that communicate(s) the inside of the processing chamber with the central passage of the inlet/outlet head outside its central tube.

The flow guide or "diverter/inverter" typically comprises a peripheral rim of external cylindrical shape that extends from the periphery of a frusto-conical upper surface of the flow guide. This peripheral cylindrical rim fits in the inner cylindrical wall of the processing chamber below the junction of the inner cylindrical wall and the inclined upper wall of the processing chamber, leaving a small space As in the known device, the processing chamber usually contains within its cylindrical wall an axially movable member such as a piston that defines a separation space of variable volume wherein the biological fluid to be processed and separated is received. Also as in the known device, the processing chamber of the device according to the invention is part of a disposable set comprising a set of containers for receiving the biological fluid to be processed and separated and the separated components, and optionally one or more additional containers for additive solutions. The device according to the invention also preferably further comprises a cabinet for receiving the processing chamber, the cabinet having drive means for driving the centrifugal processing chamber and preferably also means for controlling the axial position of an axially movable member such as a piston in the processing chamber.

The device according to the invention is also preferably provided with closure members for the inlet/outlet to the processing chamber, said closure members being clips or pinch valves that act on tubing of the disposable set, and/or stopcocks included in the disposable set and/or fitted on a cabinet for receiving the processing chamber.

Another aspect of the invention is a system for the processing and separation of biological fluids into components, comprising the device as discussed previously and further comprising at least one peristaltic pump for pumping incoming biological fluid through the inside of the central tube; and/or for pumping extracted processed biological fluid components via the central tube; and/or for pumping extracted processed biological fluid components via said outlet on the second part of the inlet/outlet head.

This system optionally comprises a first peristaltic pump operable to pump incoming biological fluid through the inside of the central tube into the processing chamber, and a second main peristaltic pump operable to pump extracted processed biological fluid components via said outlet on the second part of the adaptor head, the first and optional second peristaltic pumps being optionally operable simultaneously to provide continuous flow processing. However, continuous flow can be achieved also and preferably with a single peristaltic pump.

Another aspect of the invention is a method of processing and separating biological fluids into components using the device or the system as discussed above, the method comprising the following steps:
(a) filling the processing chamber with a biological fluid via the first inlet/outlet in the inlet/outlet head, for example an axial inlet via a central tube, with the second inlet/outlet of the inlet/outlet head closed, for example a lateral outlet on the second part of the adaptor head closed;
(b) rotating the processing chamber to centrifuge biological fluid in the chamber in order to separate different components of the biological fluid onto the inner cylindrical wall of the processing chamber or lighter or waste components into the inside of the processing chamber;
(c) operating in a continuous processing mode wherein filling of the processing chamber with a biological fluid via a first inlet/outlet, for example via a central tube, is carried out while at the same time extracting, via a second inlet/outlet, for example a lateral outlet on the second part of the inlet/outlet head, waste or light components that have separated into the inside of the processing chamber;
(d) closing of said first inlet/outlet whereby the processing chamber is no longer being filled with biological fluid, and continuing to extract components, for example via a lateral outlet; and
(e) closing of said second inlet/outlet, for example a lateral outlet whereby processed components that have separated into the inside of the processing chamber are no longer extracted via said outlet, and extracting through the first inlet/outlet, for example via said central tube, components that have separated onto the inner cylindrical wall of the processing chamber.

In this method, filling of the processing chamber with a biological fluid and/or extracting components is preferably produced by or is assisted by pumping, preferably by an external peristaltic pump, and/or by displacing in the processing chamber an axially movable member such as a piston to alter the volume of a separation space of variable volume defined by the axially movable member.

Components are preferably extracted via said second outlet by pumping, preferably with a peristaltic pump. In a preferred, embodiment during the continuous processing of step (c) biological fluid is continuously supplied to the processing chamber by pumping with a peristaltic pump, and separated components are continuously extracted by pumping with a peristaltic pump.

An advantage of the described method is that continuous processing in step (c) can be continued to process/separate a volume of biological fluid that exceeds the maximum separation volume of the processing chamber.

Just prior to and/or during step (e), the centrifugal processing chamber can be accelerated/decelerated and/or rotated in opposite directions to loosen and/or mix separated components that have adhered on the inner cylindrical wall of the processing chamber.

The centrifuging during step (b) is typically continued during steps (c) and (d), continuously or discontinuously.

BRIEF DESCRIPTION OF THE DRAWINGS

The invention will now be described by way of example with reference to the accompanying drawings, wherein:

FIG. 2 shows three views of a flow guide or diverter/inverter in plan view, side view and in perspective;

DETAILED DESCRIPTION

Figure 1A:
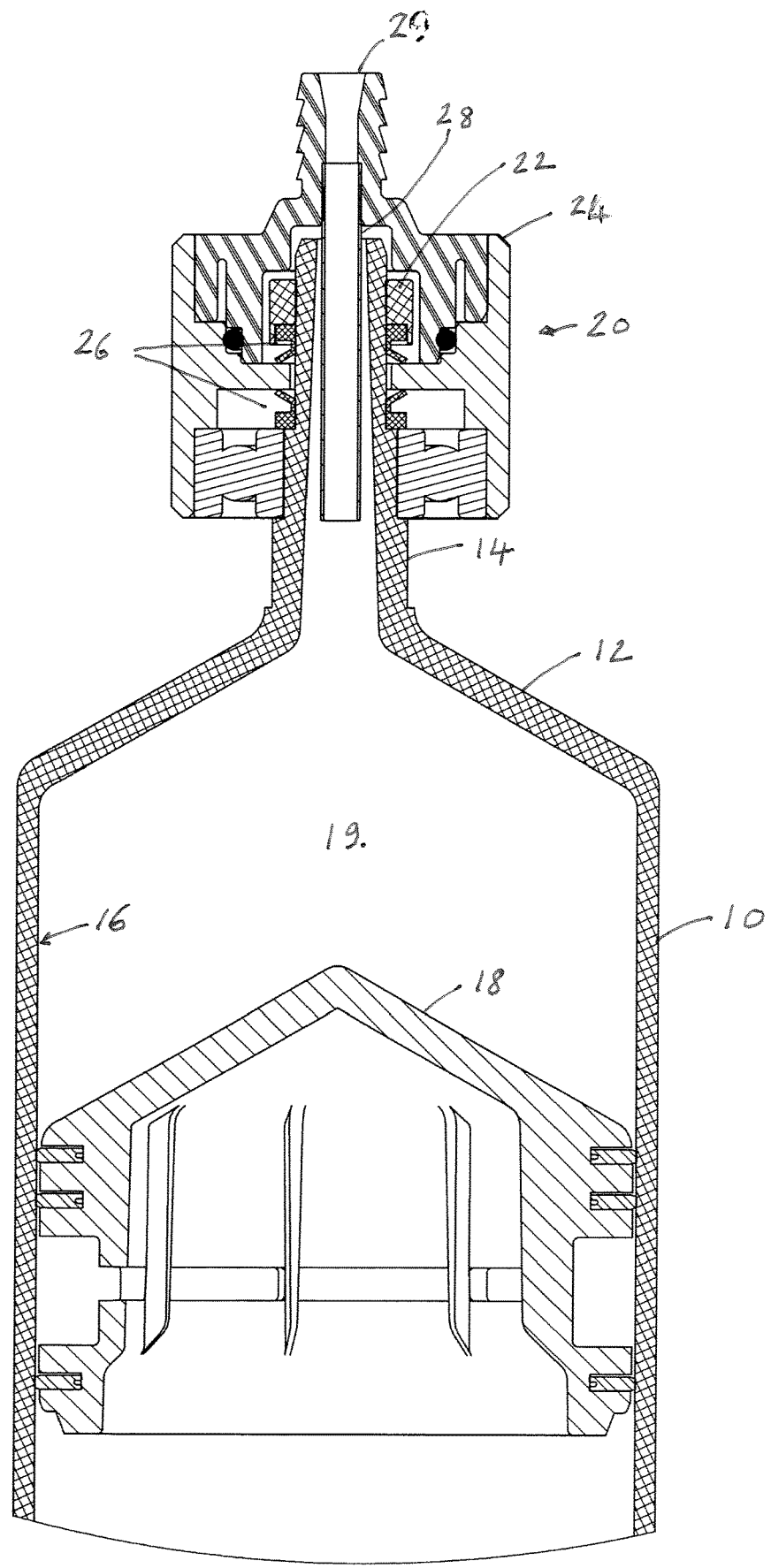
FIG. 1A is a cross section through the upper part of a processing chamber with its inlet/outlet head, according to the prior art.

FIG. 1A shows the top part of a prior art device of the type known from EP-B-0 912 250. Such known devices comprise a hollow centrifugal processing chamber 10 rotatable about an axis of rotation. The processing chamber 10 has an inner cylindrical wall 16 enclosing a space 19 for receiving biological fluids to be processed and an inclined upper wall 12 leading to a neck 14 having an inlet/outlet 29 for biological fluid to be processed and for processed components of the fluid. The space 19 in the hollow processing chamber 10 for receiving biological fluids occupies the entire uninterrupted volume across the hollow processing chamber 10 between facing parts of the inner cylindrical wall 16 along the length of the cylindrical wall. Said space has a given volume delimited by a bottom (10B, FIG. 9) of the hollow cylindrical chamber 10, or a variable volume delimited by the position of an axially movable member such as piston 18 within the cylindrical wall. A dynamic/static inlet/outlet head 20 or "rotary seal" is mounted on the neck 14. The inlet/outlet head 20 has an inner first part 22 rotatable with the processing chamber's neck 14 and an outer/upper second part 24 that remains stationary. The first and second parts 22,24 of the inlet/outlet head 20 have two double seals 26 allowing rotation of the first part 22 with the neck 14 relative to the stationary second part 24. The inlet/outlet head has a central through-passage ending with the inlet/outlet 29 for the inlet of biological fluid to be processed and the outlet of processed/separated components of the fluid. A central stationary tube 28 is held by the part 24.

The centrifugal processing chamber 10 contains within its inner cylindrical wall 16 an axially movable member namely a piston 18 that defines a separation space 19 of variable volume wherein the biological fluid to be processed and separated is received. By axially moving this member/piston 18, biological fluids can be intaken into the separation space 19 or output, via the central through-passage 29.

It can be seen that with the known device the biological fluid to be processed is intaken via the central through-passage (axial inlet/outlet 29) and the processed components are extracted also via the central through-passage (the same axial outlet/inlet 29). As mentioned previously, the quantity of biological fluid that can be processed/separated at one time is limited by the maximum volume of the separation space 19 of the known device's processing chamber 10. Consequently, a given processing chamber of the prior art cannot be used to process large volumes of biological liquid.

Figure 1B:
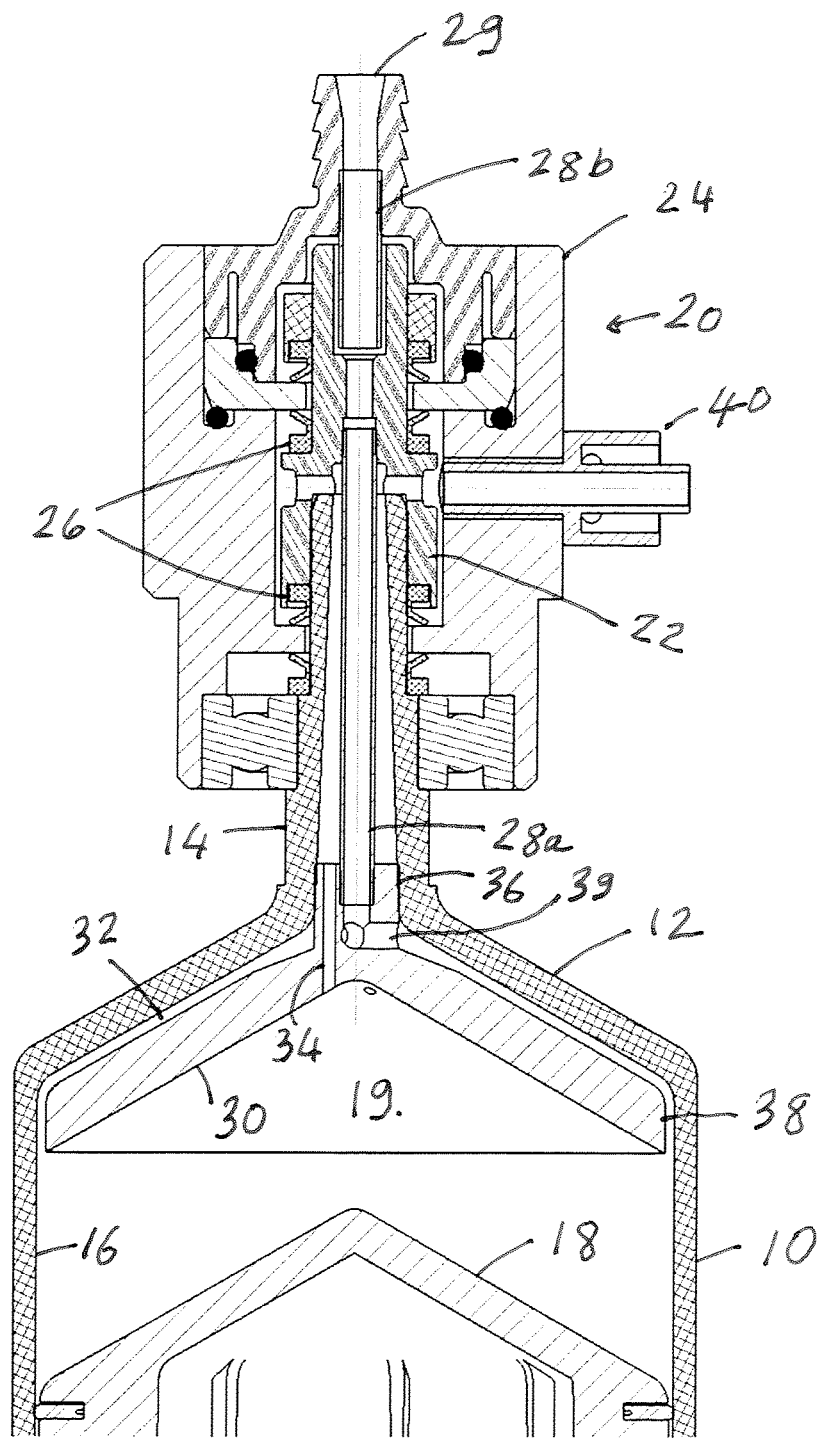
FIG. 1B is a cross section through the upper part of a processing chamber according to the present invention with its inlet/outlet head.

This limitation is overcome by the present invention. FIG. 1B shows a processing chamber of the present invention, using the same reference numerals as in FIG. 1A to designate like parts.

As shown in the example of FIG. 1B, a device according to the invention further comprises a flow guide ("diverter/inverter") 30 inserted in and rotatable with the processing chamber 10. The flow diverter/inverter 30 is located adjacent to, spaced slightly apart from and in shape-matching relationship to the inclined upper wall 12 of the processing chamber 10, leaving an inclined frusto-conical annular space 32 of several mm. A central tube in two parts, an inner part 28a and an outer part 28b, extends through the central through-passage of the inlet/outlet head 20. The central tube 28a, 28b is connected, on the one hand, to deliver incoming biological fluid through the inside of the central tube 28b, 28a and through the space 32 between the flow diverter/inverter 30 and said inclined wall 12, to the inner cylindrical wall 16 of processing chamber 10 and, on the other hand, to extract processed fluid components separated at the inclined wall 16 of processing chamber 10 and that pass through the space 32 between the flow diverter/inverter 30 and said inclined upper wall 12.

In this improved device, the inside part 19 of the processing chamber located beyond (i.e. below) the flow diverter/inverter 30 is in fluid communication via an aperture 34 in the central part of the flow diverter/inverter 30 to the central through-passage of the inlet/outlet head 20 outside said central tube 28a.

Also, the outer stationary second part 24 of the inlet/outlet head 20 has a lateral outlet 40 for the extraction of processed biological fluid components from the inside 19 of the processing chamber 10, said lateral outlet 40 being in fluid communication with said central through-opening 29 of the inlet/outlet head 20 outside said central tube 28a.

In this embodiment, the processing chamber's upwardly-projecting elongated central neck 14 extends into the inside of the rotatable first part 22 of the inlet/outlet head 20 up to adjacent the level of the lateral outlet 40. Also, in this case, the sealing means of the inlet/outlet head 20 comprise two first seals 26 located axially on one side of the lateral outlet 40 and two second seals 26 located axially on the other side of the lateral outlet 40.

The central tube 28a, 28b comprises a stationary axially-outer part 28b extending in the stationary second part 24 of the inlet/outlet head 20, and a rotatable axially-inner part 28a connected to a central part of the flow diverter/inverter 30. The inner part of the central tube 28a communicates with the space 32 between the flow diverter/inverter 30 and the inclined upper wall 12 via openings 39.

The rotatable first part 22 of the inlet/outlet head 20 is located laterally inside the stationary second part 24 of the inlet/outlet head, and inside the stationary outer end.

As usual, the inclined upper wall 12 of the processing chamber 10 is frusto-conical as is the upper surface of the flow diverter/inverter 30. As shown, the flow diverter/inverter 30 has an upwardly-protruding central sleeve 36 that fits in the neck 14 of the processing chamber 10 leaving the space 32 of several millimeters between the facing frusto-conical surfaces. The lower end of the central tube 28a fits in this central sleeve 36 and communicates with said space 32 via openings 39 in sleeve 36. In this example, the flow diverter/inverter 30 has an aperture in the form of at least one axially-directed through passage 34, preferably three equally-distributed axial through passages 34 (FIG. 2), in its central sleeve 36 that communicate(s) the inside 19 of the processing chamber 10 with the central passage of the inlet/outlet head 20 outside its central tube 28a.

The flow diverter/inverter 30 typically comprises a peripheral rim 38 of external cylindrical shape that extends from the periphery of a frusto-conical upper surface of the flow diverter/inverter 30. This peripheral cylindrical rim 38 fits in the inner cylindrical wall 16 of the processing chamber 10, below the junction of the inner cylindrical wall 16 and the inclined upper wall 12, leaving a space.

Figures 1C, 1D:
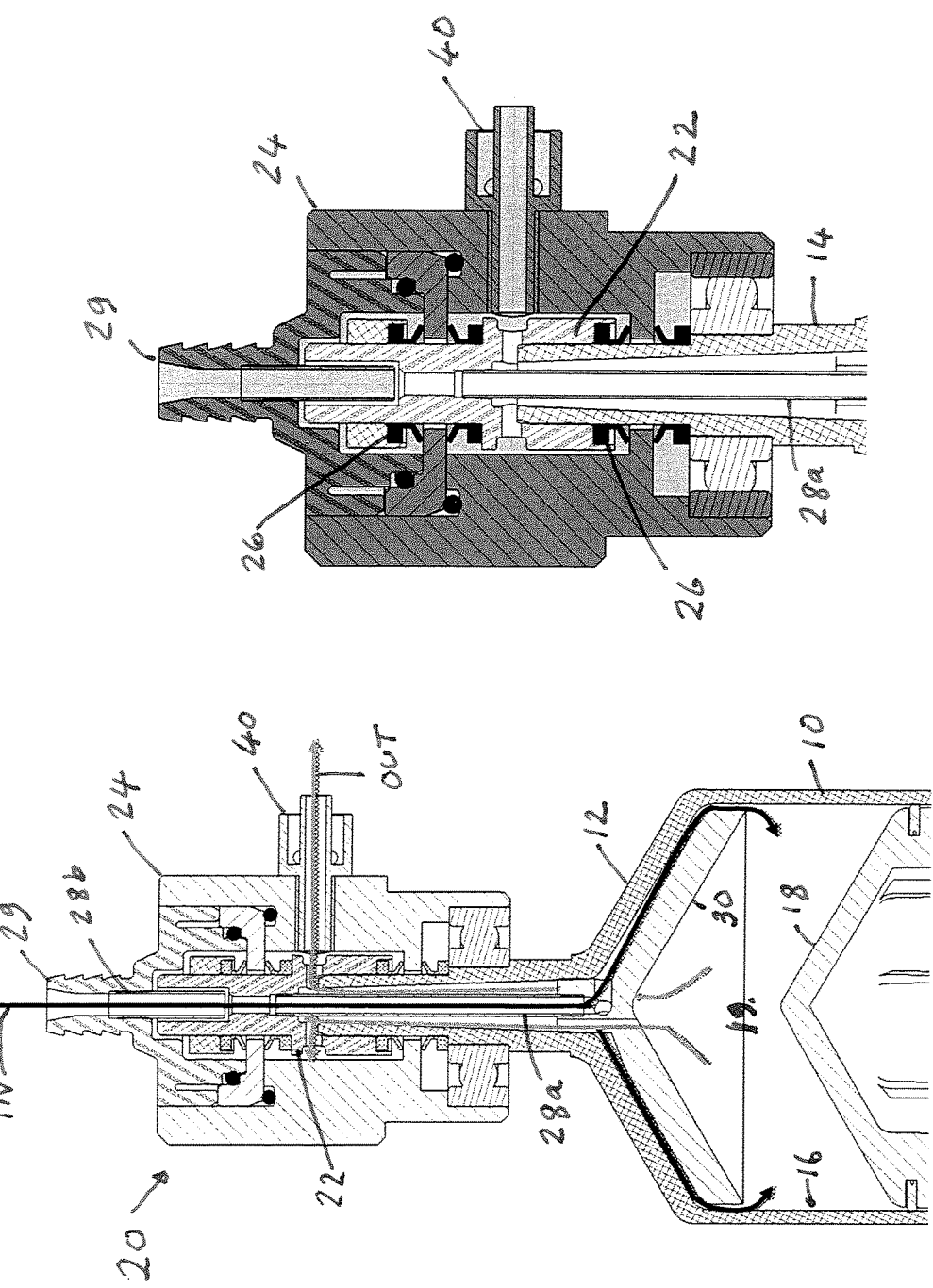
FIG. 1C is a view of the inventive processing chamber, like FIG. 1B, schematically showing the flow of incoming biological fluid and of outgoing processed components.
FIG. 1D is a view of the inlet/outlet head of the inventive processing chamber, like FIG. 1B, schematically showing the stationary and rotating parts.

FIG. 1C shows the flow of biological fluid entering and exiting the processing chamber 10. First the biological fluid enters the chamber through the inlet port 29 situated in the middle-top part. The fluid falls down by passing first through the static part 24 of the inlet/outlet head 20, then continuing through the dynamic part 22 potentially in rotation, and then reaching the flow diverter/inverter 30. The flow diverter/inverter 30 forces the fluid to continue its way from the central axial to the external side of the conical chamber 10 in rotation, all as shown by the dark line "IN". This ensures a smooth transition for cells that switch from a static to a spinning mode and potentially subject to a high centrifugation force.

The biological fluid inside the processing chamber 10 is then centrifuged, and biological cells are separated from supernatant or other medium, by a density physical principle after being exposed to a horizontal sedimentation force. Cells remain compacted at the external side of the chamber 10 at the inner cylindrical wall 16, while supernatant or medium can be removed via the central axis. As indicated by the gray arrow "OUT", the fluid to be discarded is then pumped from the bottom-central axis of the chamber (centre of space 19), passes through the apertures 34 in the centre of the diverter/inverter 30, and goes up outside the tube 28a in rotation. Then, after being aspirated up to the height of the lateral outlet 40, the separated biological fluid to be discarded is extracted through the lateral outlet 40 in the static part 24 of the inlet/outlet head. The discarded biological fluid thus switches from a high spinning mode to a static mode. The working of this mechanical mechanism might potentially be damaging for cells. By damaging, is meant creating a pressure, friction, sheer force or even cutting cells by the spinning mechanical part that will either potentially differentiate stem cells making them losing their totipotent properties, or even kill them by apoptosis, necrosis or other destructive mechanisms. For this reason, it is ensured that only discarded product with no cells or with only a low cell concentration are going through the described pathway.

FIG. 1D illustrates the static and dynamic part of the inlet/outlet head 20 of the processing chamber, with airtightness or water tightness provided via seals 26. The central light part 22 indicates the dynamic mechanical pieces that will spin during a normal procedure. The external dark part 24 indicates the static mechanical pieces that will not spin during a procedure. Tightness is ensured through four seals 26 represented in black.

FIG. 2 illustrates the design of the flow diverter/inverter 30. The upper conical surface has the same shape and dimensions as the internal surface of the inclined upper wall 12 of the processing chamber. When assembled, a small canal or space 32 of few millimetres remains for allowing the fluid to pass through. In the centre, the central aperture 35 in the central sleeve 36 is connected by laterally-oriented apertures 39 leading in to the space 32 between the frusto-conical surfaces. This diverts the fluid and forces the biological fluid to flow down on the conical upper part. The three apertures 39 at 120 degrees each and at a distance of few millimetres ensure that central fluid in the chamber is pumped up through the external side of the dynamic part 22, and thus reaching the lateral outlet port 40.

FIG. 3 illustrates design variants of the continuous flow processing chamber.

Figure 3A:
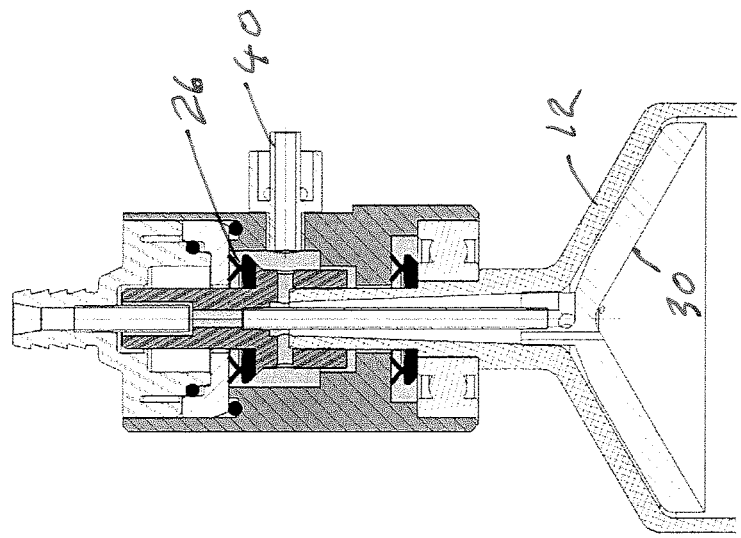
FIG. 3a, FIG. 3b and FIG. 3c show variants of the continuous flow processing chamber.

FIG. 3a is a variant of the flow diverter/inverter 30 that could be used in case the flow does not need to be inverted. In this design, the inlet port 29 will downwardly deliver the biological fluid entering via the middle of the centrifugal chamber, while the outlet port 40 is connected with the path situated in the side of the internal chamber, i.e. via the inclined annular space 32. This drawing removes the inverted flow path. The inlet port 29 is connected with the central axis of the chamber, and the outlet port 40 is connected with side channels or space 32 of the chamber. Continuous flow processing is the same, only the inlet/outlet port connections are inverted.

Figure 3B:
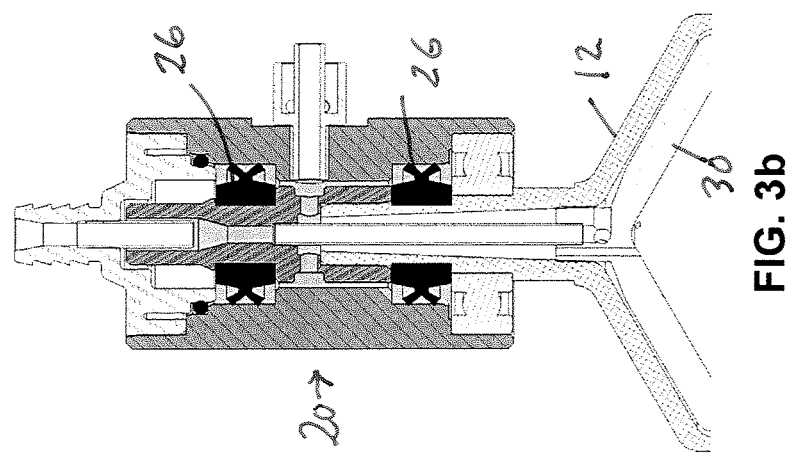

FIG. 3b simplifies the design by using only two seals 26 for ensuring tightness instead of four seals. Each seal 26 has two radially-directed lips that will ensure tightness when pressure or vacuum is generated by the intermediary of a peristaltic pump or up and down movement of the piston.

Figure 3C:
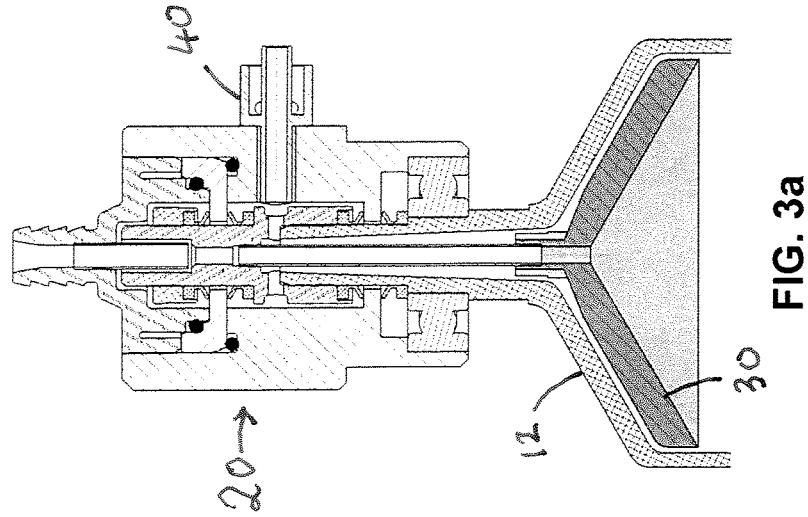

FIG. 3c is design variant of the two seals 26 each having two axially-directed lips aligned as shown for ensuring tightness as described in relation with FIG. 3b.

Disposable Kits

Figure 4A:
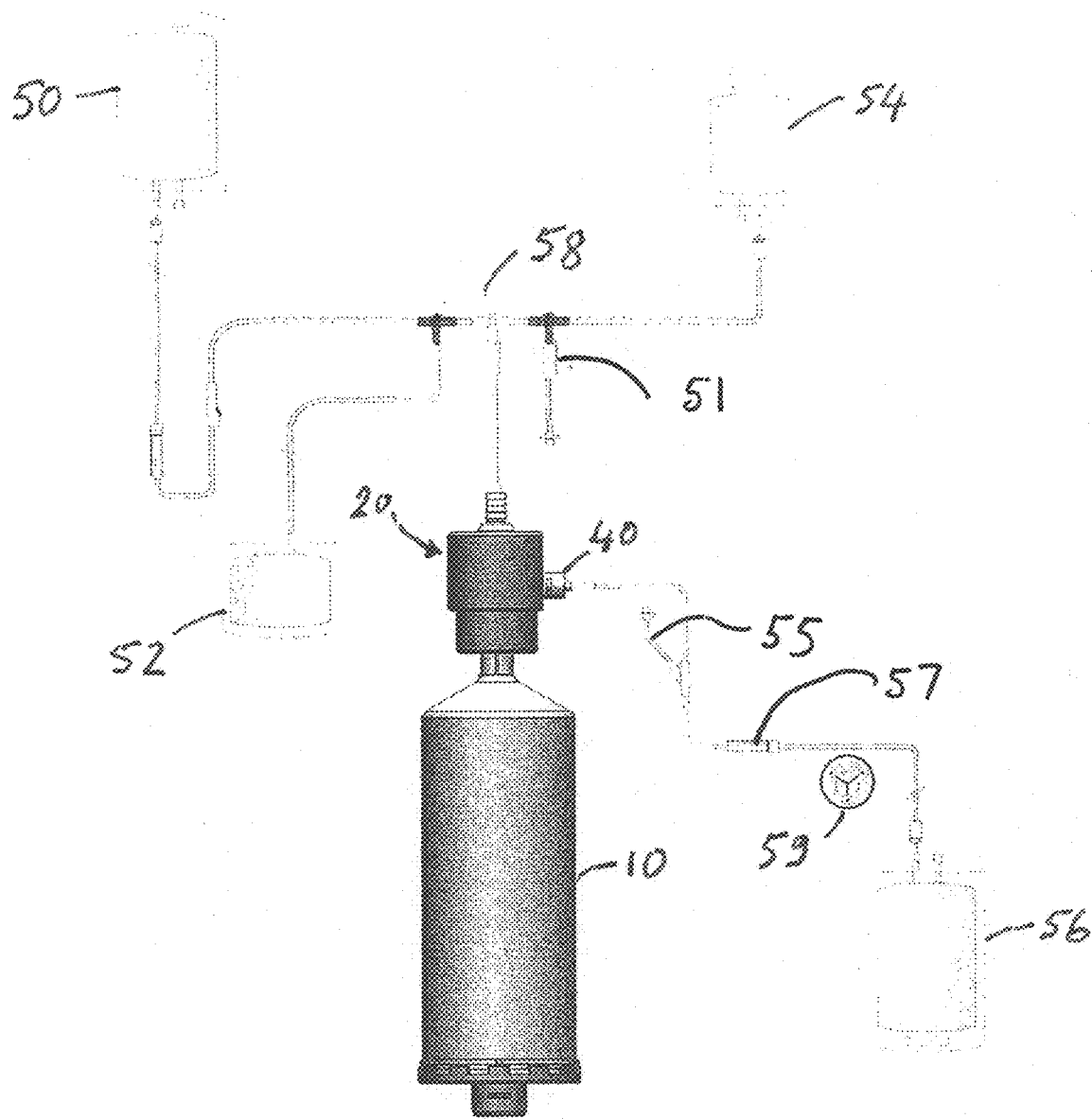
FIG. 4A and FIG. 4B show two examples of disposable sets including the processing chamber of the present invention.

FIG. 4A shows a typical disposable kit that will be used with the inventive processing chamber 10/20/40. On the upper-left, a bag 50 containing a volume to be processed is connected to the disposable kit. On the bottom-left, a collection bag 52 is attached to the kit for collecting concentrated cell solutions. On the top-right side, a bag 54 is optionally connected to the disposable kit and may contain washing solution for rinsing the chamber at the very end of the procedure, or eventually for suspending concentrated cell solution in a nutritive solution. On the bottom-right, a waste bag 56 is used for discarding solution that has to be eliminated from cells.

A buffer 51 containing a filter is inserted in the input line, having the aim to filter aggregates or other unwanted material from the volume to process, and also preventing air bubbles that could flow inside the processing chamber. In addition, a stopcock ramp 58 is used for switching between the multiple bags, or eventually for priming air if necessary through an air filter for ensuring sterility. The disposable set can also include pinch valves located on the tubing for controlling the opening/closing of the tubes.

On the waste line, an air filter 55 for connecting to a pressure sensor is used for monitoring constantly the maximum pressure or vacuum applied inside the disposable set. Also a peristaltic pump 59 is connected on the waste line, and will generate the flow by minimally potentially damaging cells that will not circulate through the pump mechanism.

An air buffer 57 is preferably connected between the lateral outlet 40 of the processing chamber and the peristaltic pump 59. This air buffer 57 has a role of limiting pressure jerks when the peristaltic pump 59 is operated. The air buffer can be a drip chamber.

As shown, the waste line leading to wastebag 56 is connected to the lateral outlet 40 of the processing chamber's inlet/outlet head 20.

Figure 4B:
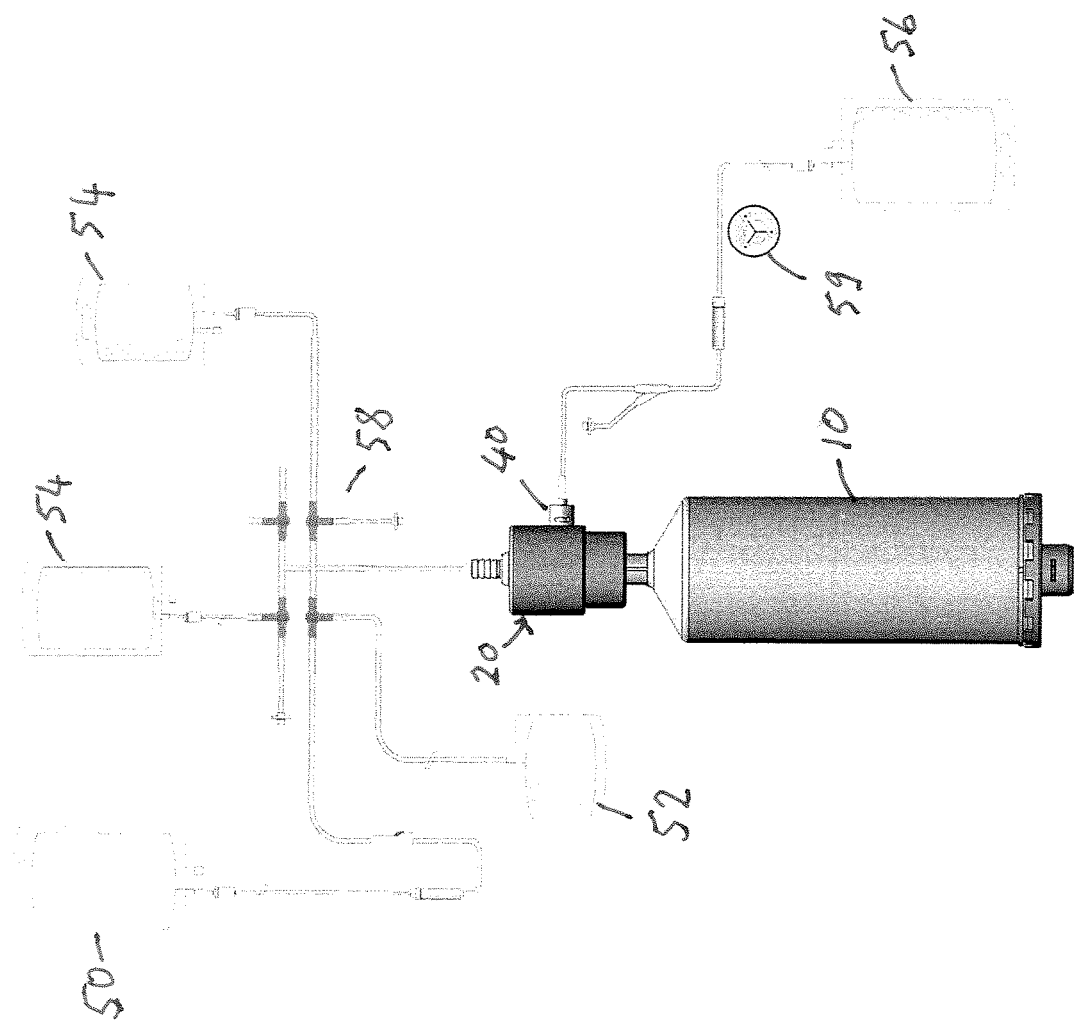

FIG. 4B illustrates a similar disposable kit that has multiple input-output and is able to process and switch between more biological solutions. Bag selection is done through eight stopcocks 58 ensuring up to eight input or output bags.

Figure 5:
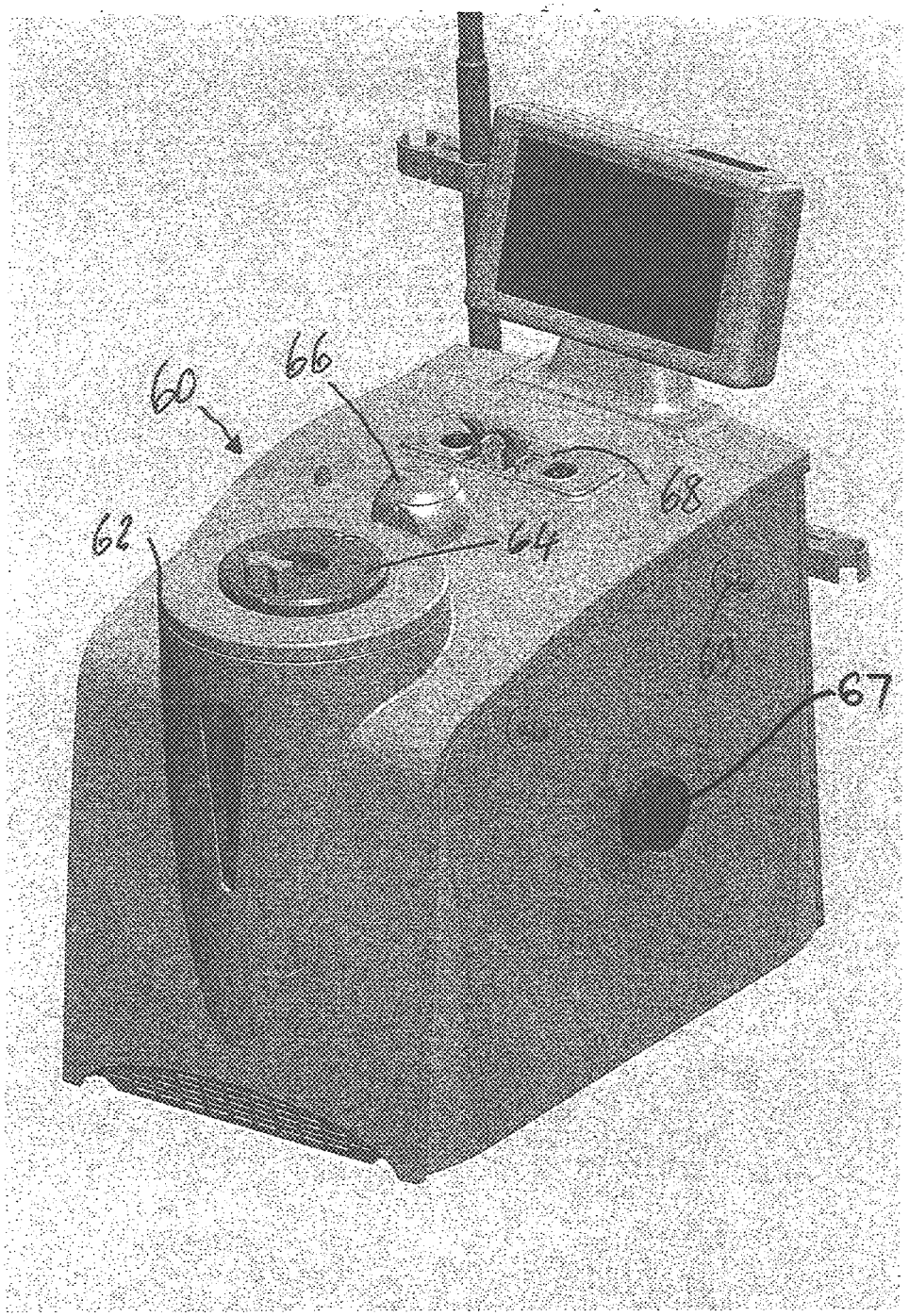
FIG. 5 is a perspective view of a cabinet for receiving a processing chamber of the present invention.

FIG. 5 shows a modified version of the cabinet of a known system that integrates a peristaltic pump. As shown the system comprises a cabinet 60 including profiled front part 62 for receiving a centrifugal processing chamber via swing-opening plates 64. The cabinet top also incorporates a spectrometric sensor 66 including bubble detection working with ultrasound technology for measuring biological elements and air bubbles flowing to the processing chamber. A control 67 for a peristaltic pump is located on the cabinet side and a stopcock motor control 68 on its top. On its sides the cabinet also has hooks 69 for attaching tubing of an installed disposable set.

This system works in accordance with the disposable kit illustrated in FIG. 4A. In addition, for a proper calculation of air bubbles entering the processing chamber, an incorporated optical line sensor can integrate an additional ultrasound emitter and receptor that is able to calculate real-time volume of air passing through the tube.

Figure 6:
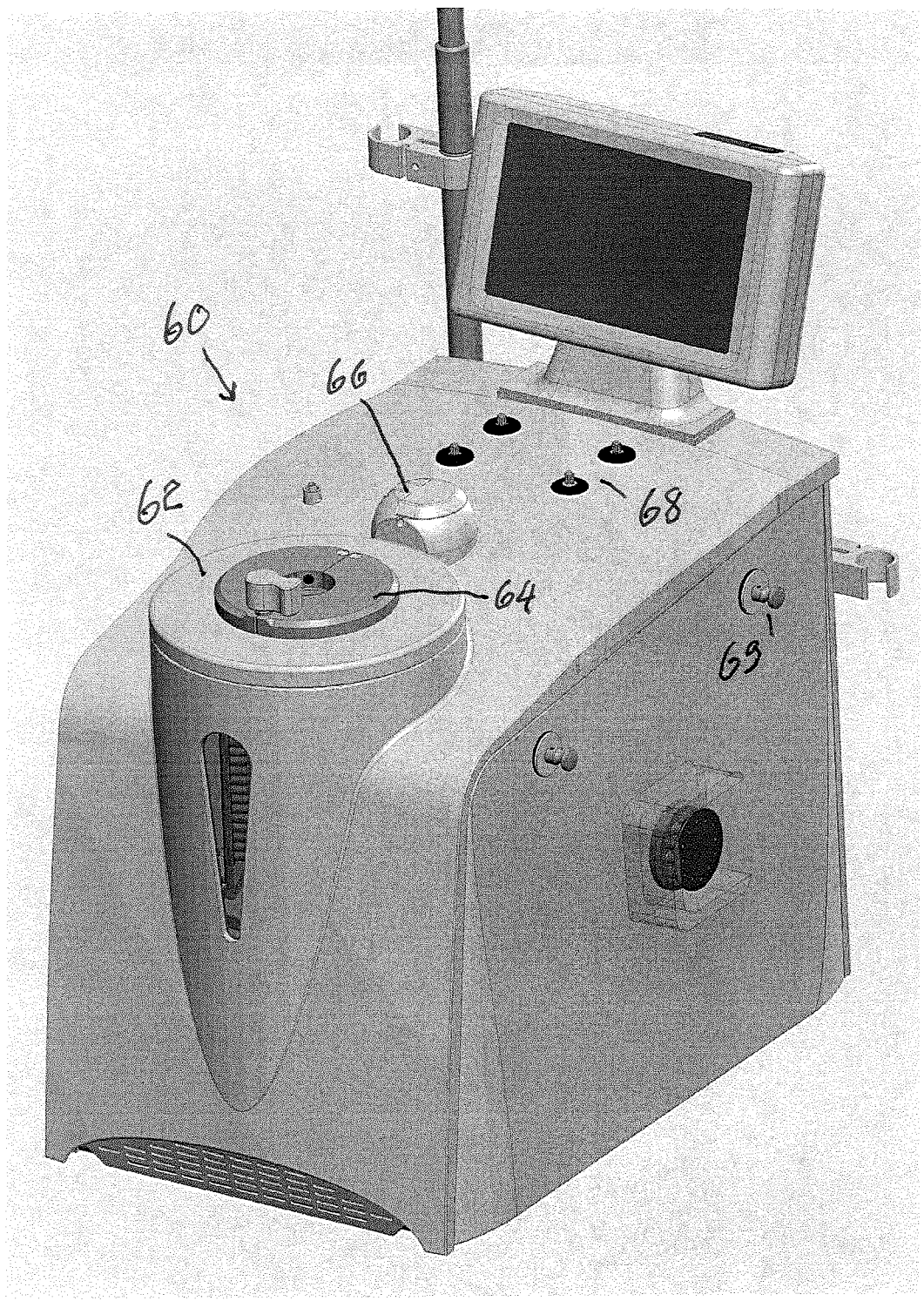
FIG. 6 is a perspective view of another cabinet for receiving a processing chamber of the present invention.

FIG. 6 shows a modified version of the same system that integrates a peristaltic pump and four stopcock motors with individual controls 68. This system works in accordance with the disposable kit illustrated in FIG. 4B.

The continuous processing flow function achievable with the device according to the invention is mainly ensured via one or more external peristaltic pumps generating the flow, on the one hand through the inlet port 29 pumping the biological fluid to the external rotating side 16 of the processing chamber where the sedimentation G force is at maximum and, on the other hand, through the lateral outlet port 40 situated in the centre of the processing chamber's inlet/outlet head 20 for removing plasma, supernatant or other unwanted biological fluid of lower densities where there is no or little sedimentation force applied. By combining this functionality with a variable processing volume for example as described in EP-B-0 912 250, this invention solves existing limitations of small volume collection of concentrated cells starting from large volume biological fluids.

The Main Processing Sequence

Figure 7:
FIG. 7 is a flow diagram of the main processing sequence, showing the sequential relationship of different phases of operation illustrated in FIG. 8A, FIG. 8B, FIG. 8C, FIG. 8D and FIG. 8E below.

A main application of the invention relates to the fast volume reduction of large biological fluid into a small collection of concentrated cells, as illustrated in FIG. 8A to FIG. 8E. The flow-diagrams of FIG. 7A and FIG. 7B set out the processing steps corresponding to each of FIG. 8A to FIG. 8E.

Figure 8:
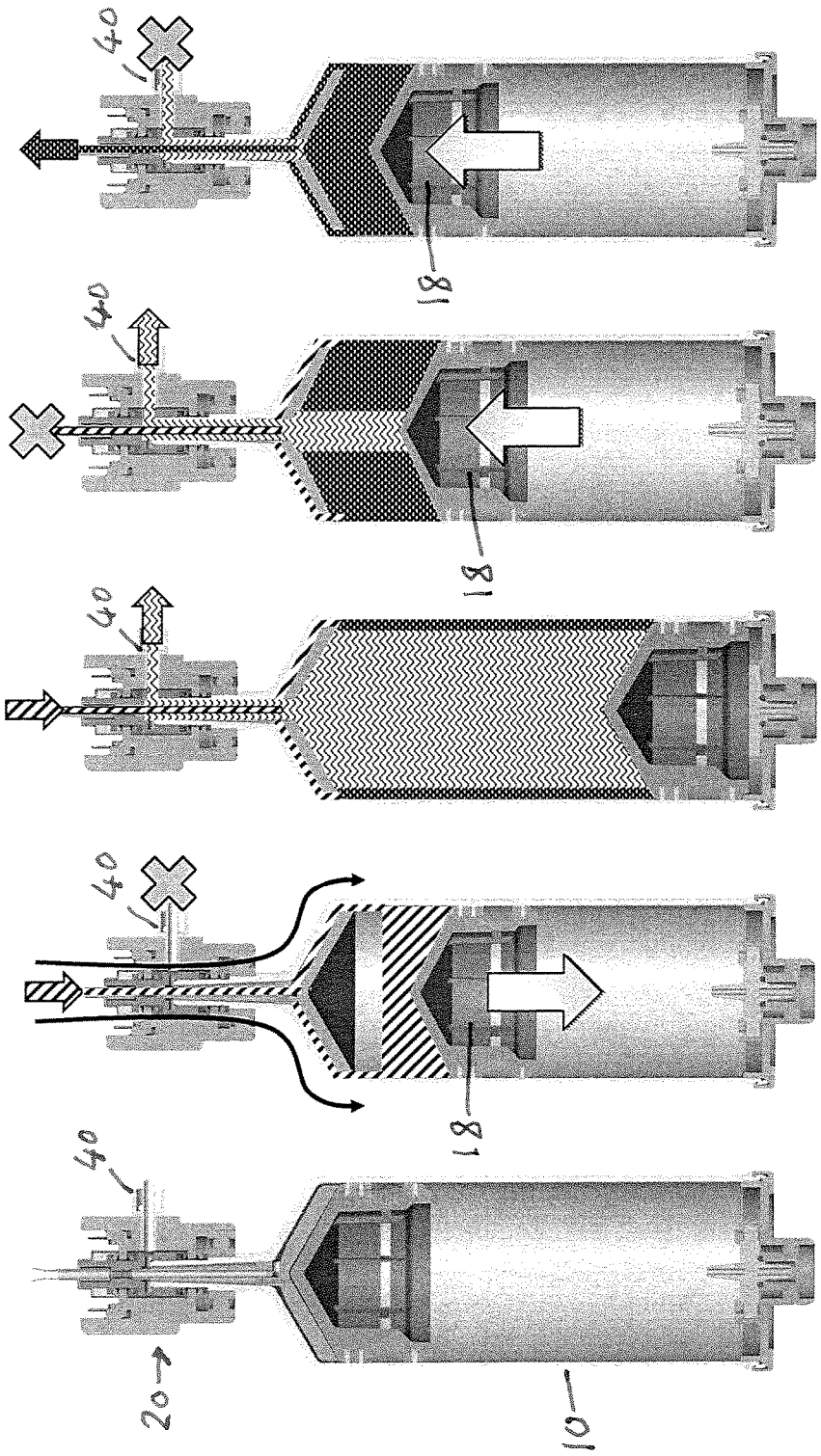
FIG. 8A, FIG. 8B, FIG. 8C, FIG. 8D and FIG. 8E schematically show a processing chamber according to the present invention during different phases of operation.

The first step consists of inserting the centrifugal processing chamber 10 inside the equipment with inlet and outlet ports 29, 40 closed, as shown in FIG. 8A. Then, filling of the centrifugal chamber 10 by pumping into it the volume to be processed can start, FIG. 8B. After connecting the inlet port 29 with the biological fluid to be processed, the mechanism of aspirating down the piston 18 by the intermediary of a pneumatic system that creates a vacuum is done as described in EP-B-0 912 250. During filling, there is potentially a need to remove remaining air that may have stayed trapped in the processing chamber 10. For performing this action, the piston 18 can be pushed slightly up by generating compressed air pressure below the moveable piston. Remaining air and a small portion of filled volume will be re-extracted in the volume to be processed. Then filling can start again until the piston 18 reaches the bottom side of the processing chamber 10.

As indicated in FIG. 8B, during filling the axial inlet 29 is open and the lateral outlet 40 is closed.

At this point, the separation space of processing chamber 10 is filled with a biological solution and sedimentation can start. Sedimentation process is done through centrifugation of the disposable set, as described for example in EP-B-1 144 026.

After some time of centrifugation at a certain rotating speed, blood or biological cells are separated from supernatants or medium solution and the continuous flow for large volume separation can start, as shown in FIG. 8C. In this state, the lateral outlet port 40 is connected with a waste bag and an external peristaltic pump connected on the waste line is activated. There is the possibility that trapped air still remains in the channel of the outlet port 40, but it will be expelled in the waste bag as soon as peristaltic pumps will be activated. Now, the biological fluid is continuously pumped and separated from the initial volume connected to the inlet port 29 of the chamber, by being centrifuged in the separation chamber in rotation, and finally with supernatant being removed from the central axis of the processing chamber and redirected to the waste bag through the outlet port. During the entire separation process, biological cells will remain in the processing chamber 10, and the speed flow is calculated in order to ensure a sufficient time for the cells to be exposed to a separation force that will guarantee a good separation.

As indicated in FIG. 8C, during continuous processing, the axial inlet 29 is open for the continuous intake of biological fluid, and the lateral outlet port 40 is open for the continuous removal of separated waste.

Once the desired volume has been entirely processed, the peristaltic pump(s) stop. At the beginning of the procedure, the user has set a requested final volume in the software user interface of the system, so at this stage the inlet port 29 is closed and the piston 18 starts moving up by applying the same air-pressure mechanism as described previously, as shown in FIG. 8D (axial inlet 29 closed; lateral outlet port 40 open). During this stage, rotating speed is maintained to ensure proper cell separation, and piston 18 moves up at a validated rotation speed and discards the remaining volume into the waste bag until the final volume desired corresponds to the remaining volume in the processing chamber 10.

The last stage is the recovery procedure of the concentrated cells, shown in FIG. 8E. The remaining cell solution in the disposable chamber 10 is firstly mixed through several motor acceleration/decelerations on both directions in order to detach/mix cells potentially stuck on the inner plastic walls 16 of the disposable chamber 10. Then, the inlet port 29 is opened while the outlet port 40 is closed, and piston 18 starts extracting concentrated cells via the axial inlet/outlet port 29. By doing so, cells never pass through the peristaltic pump mechanism that could cause some mechanical stress on the biological cells or stem cells. In addition, for ensuring a proper extraction of cells out of the processing chamber, a dilution phase can also be performed by pumping a small amount of washing solution or suspension buffer in the centrifugal chamber 10, by mixing the solution again and then extracting the solution in the final desired solution. By doing so, cell losses are minimized.

Variant of the Processing Chamber Without a Piston

Figure 9:
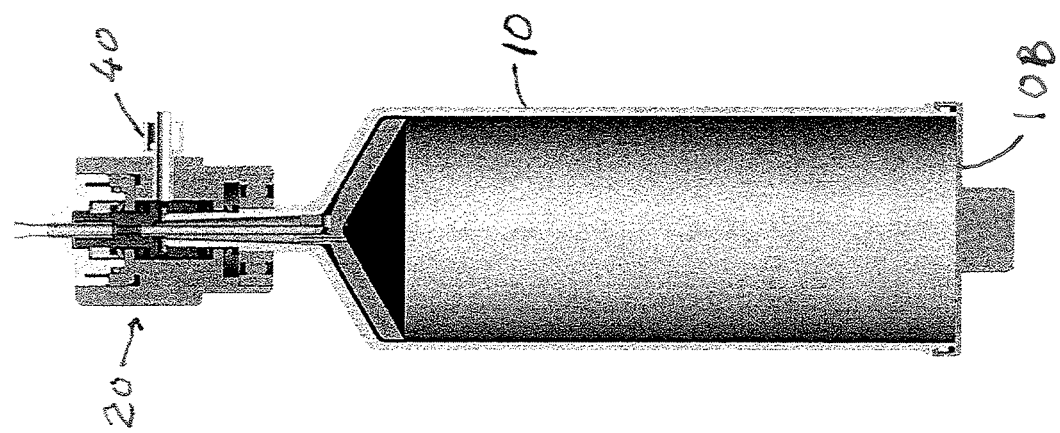
FIG. 9 shows a variant of the processing chamber without a piston.

FIG. 9 shows a variant of the processing chamber 10 whose cylindrical wall extends to a bottom wall 10B providing an inner space of fixed volume for receiving biological fluids to be processed. The upper part (inlet/outlet head 20) has the same design as before 10 but the processing chamber 10 does not contain a moveable piston for providing a variable volume.

This chamber 10 of given volume is able to process large volumes through a continuous flow where the final volume to be collected is equal to the processing chamber volume. The chamber 10 can be used with same cabinet and disposable kits as described previously. This variant of the invention greatly simplifies the technology as no pneumatic system is needed anymore for moving a piston up and down, and no infrared detection system is needed for detecting real-time volume remaining in the processing chamber. With this variant, peristaltic pumps are used to intake biological fluid and output separated components.

The invention claimed is:

1. A device for processing and separating biological fluids into components, comprising:
a hollow centrifugal processing chamber rotatable about an axis of rotation, the processing chamber having an inner cylindrical wall enclosing a separation space for receiving biological fluids to be processed and having an inclined upper wall leading to a narrower neck that extends axially from the cylindrical wall and its inclined upper wall, the cylindrical wall, its inclined upper wall and the narrower neck all being in one piece, wherein the space in the hollow processing chamber for receiving biological fluids occupies the entire volume across the hollow processing chamber between facing parts of the inner cylindrical wall and along the length of the cylindrical wall, said space having a given volume delimited by a bottom of the hollow cylindrical chamber, or a variable volume delimited by the position of an axially movable member within the cylindrical wall; and
an inlet/outlet head mounted on and around the neck of the processing chamber, the inlet/outlet head having a first part rotatable with the processing chamber and a second part that remains stationary, the first and second parts of the inlet/outlet head being connected by a sealing means allowing rotation of the first part relative to the second part, the inlet/outlet head having a central through-passage for the inlet of biological fluid to be processed and the outlet of processed/separated components of the fluid;
a flow guide inserted in and rotatable with the processing chamber, the flow guide being located adjacent to, spaced slightly apart from and in shape-matching relationship to the inclined upper wall of the processing chamber to define with the inclined upper wall of the processing chamber an inclined flow passage, the flow guide being disposed above said separation space for receiving biological fluids to be processed with its inclined flow passage leading into a top part of the inner cylindrical wall of the processing chamber; and
wherein the inlet/outlet head comprises:
a first inlet/outlet and a second inlet/outlet, the first and second inlets/outlets being disposed on the stationary second part of the inlet/outlet head at a top end and/or at a lateral side thereof,
an axial separator in the central through-passage of the inlet/outlet head, the axial separator defining separate first and second axially-directed passages in the inlet/outlet head,
an upper part of one of the first and second axially-directed passages communicating with one of the first and second inlets/outlets, and an upper part of the other of the first and second axially-directed passages communicating with the other of the first and second inlets/outlets, and
a lower part of one of the first and second axially-directed passages communicating with said space in the processing chamber for receiving biological fluids to be processed, and a lower part of the other of the first and second axially-directed passages communicating with the inclined flow passage between the flow guide and the inclined upper wall of the processing chamber,
arranged so the device is operable in a continuous flow mode in which biological fluid to be processed can be input via one of the first and second inlets/outlets, while processed biological fluid is simultaneously output via the other of the first and second inlets/outlets.

2. The device according to claim 1, wherein the stationary second part of the inlet/outlet head comprises an external generally cylindrical body, said first inlet/outlet is an axial inlet/outlet in the inlet/outlet head, and said second inlet/outlet is a lateral inlet/outlet located in a lateral side of the generally cylindrical body.

3. The device according to claim 2, wherein the processing chamber's upwardly-projecting elongated central neck extends into the inside of the rotatable first part of the inlet/outlet head up to adjacent the level of the lateral inlet/outlet.

4. The device according to claim 2, wherein the sealing means of the inlet/outlet head comprise a first seal located axially on one side of the lateral inlet/outlet and a second seal located axially on the other side of the lateral inlet/outlet.

5. The device according to claim 1, wherein said axial separator is a central tube that comprises a stationary axial-outer part extending in the stationary second part of the inlet/outlet head, and a rotatable axial-inner part connected to a central part of the flow guide, said rotatable axial-inner part of the central tube communicating with the inclined flow passage between the flow guide and said inclined upper wall of the processing chamber.

6. The device according to claim 1, wherein the rotatable first part of the inlet/outlet head is located inside the stationary second part of the inlet/outlet head.

7. The device according to claim 5, wherein:
(i) the inclined upper wall of the processing chamber is frusto-conical as is the upper surface of the flow guide;
(ii) the flow guide has a central sleeve that fits in the neck of the processing chamber leaving a space of several millimeters forming the inclined flow passage between the facing frusto-conical surfaces;
(iii) the axial-inner part of the central tube fits in the central sleeve of the flow guide and communicates with the inclined flow passage between the facing frusto-conical surfaces; and
(iv) the flow guide comprises an aperture in the form of at least one through passage in its central sleeve that communicate(s) the inside of the processing chamber with the central passage of the inlet/outlet head outside its central tube.

8. The device according to claim 1, wherein the flow guide comprises a peripheral rim of external cylindrical shape that extends from the periphery of a frusto-conical upper surface of the flow guide, said peripheral cylindrical rim fitting in the inner cylindrical wall of the processing chamber below the junction of the inner cylindrical wall and the inclined upper wall of the processing chamber.

9. The device according to claim 1, wherein the axially movable member is a piston that defines a separation space of variable volume wherein the biological fluid to be processed and separated is received.

10. The device according to claim 1, wherein the processing chamber is part of a disposable set comprising a set of containers for receiving the biological fluid to be processed and separated and the separated components, and optionally one or more additional containers for additive solutions.

11. The device according to claim 1, further comprising a cabinet for receiving the processing chamber, the cabinet having drive means for driving the centrifugal processing chamber and also means for controlling the axial position of the axially movable member in the processing chamber.

12. The device according to claim 11, further comprising closure members for the inlet/outlet to the processing chamber, said closure members being clips or pinch valves that act on tubing of a disposable set, and/or stopcocks included in the disposable set and/or fitted on the cabinet for receiving the processing chamber.

13. A system for the processing and separation of biological fluids into components, comprising the device of claim 1 and further comprising at least one peristaltic pump for pumping incoming biological fluid through one of the first and second inlets/outlets; and/or for pumping extracted processed biological fluid components through the other of the first and second inlets/outlets.

14. A method of processing and separating biological fluids into components using the device according to claim 1, the method comprising the following steps:
(a) filling the processing chamber with a biological fluid via the first inlet/outlet with the second inlet/outlet closed;
(b) rotating the processing chamber to centrifuge biological fluid in the chamber in order to separate different components of the biological fluid into a first set of components forced towards and then onto the inner cylindrical wall of the processing chamber and a second set of components that remained inside of the processing chamber;
(c) operating in a continuous processing mode wherein filling of the processing chamber with a biological fluid is carried out while at the same time extracting, via the second inlet/outlet the second set of components;
(d) closing the first inlet/outlet to stop filling the processing chamber with biological fluid, and continuing to extract the second set of components via said second inlet/outlet; and
(e) closing said second inlet/outlet whereby the second set of components are no longer extracted via said second inlet/outlet, and extracting via said first inlet/outlet the first set of components from the inner cylindrical wall of the processing chamber.

15. The method according to claim 14, wherein filling of the processing chamber with a biological fluid is produced by or is assisted by pumping, using an external peristaltic pump and/or by displacing in the processing chamber the axially movable member to alter the volume of the separation space of variable volume defined by the axially movable member.

16. The method according to claim 14, wherein components are extracted from the processing chamber by pumping, using a peristaltic pump.

17. The method according to claim 14, wherein continuous processing in step (c) is continued to process/separate a volume of biological fluid that exceeds the maximum separation volume of the processing chamber.

18. The method according to claim 14, wherein just prior to and/or during step (e) the centrifugal processing chamber is accelerated/decelerated and/or rotated in opposite directions to loosen and/or mix separated components that have adhered on the inner cylindrical wall of the processing chamber.

19. The method according to claim 14, wherein centrifuging during step (b) is continued during steps (c) and (d), continuously or discontinuously.

20. The device according to claim 7, wherein the at least one through passage of the aperture of the flow guide comprises three equally-distributed through passages.

* * * * *